(12) United States Patent
Lindhe (10) Patent No.: US 10,383,746 B2
(45) Date of Patent: Aug. 20, 2019

(54) PROSTHETIC FOOT DEVICE

(71) Applicant: C LindheXtend AB, Halmstad (SE)

(72) Inventor: Christoffer Lindhe, Halmstad (SE)

(73) Assignee: C LindheXtend AB, Halmstad (SE)

( * ) Notice: Subject to any disclaimer, the term of this patent is extended or adjusted under 35 U.S.C. 154(b) by 0 days.

(21) Appl. No.: 15/517,369

(22) PCT Filed: Oct. 6, 2015

(86) PCT No.: PCT/SE2015/051059
§ 371 (c)(1),
(2) Date: Apr. 6, 2017

(87) PCT Pub. No.: WO2016/056983
PCT Pub. Date: Apr. 14, 2016

(65) Prior Publication Data
US 2017/0304082 A1    Oct. 26, 2017

(30) Foreign Application Priority Data

Oct. 10, 2014   (SE) ........................ 1451220

(51) Int. Cl.
*A61F 2/50*   (2006.01)
*A61F 2/66*   (2006.01)

(52) U.S. Cl.
CPC .............. *A61F 2/66* (2013.01); *A61F 2/5044* (2013.01); *A61F 2/5046* (2013.01);
(Continued)

(58) Field of Classification Search
CPC .. A61F 2/5044; A61F 2/66; A61F 2002/5053; A61F 2002/5055;
(Continued)

(56) References Cited

U.S. PATENT DOCUMENTS 3,754,286 A   8/1973   Ryan
4,547,913 A   10/1985  Phillips
(Continued)

FOREIGN PATENT DOCUMENTS

CA   2127691 A1   5/1994
FR   2734151 A1   5/1995
(Continued)

OTHER PUBLICATIONS

Trias. Ottobock Catalog. pp. 102-103. 2013.*
(Continued)

*Primary Examiner* — Christie L Bahena
(74) *Attorney, Agent, or Firm* — Renner, Otto, Boisselle & Sklar, LLP (57) ABSTRACT

A prosthetic foot device (1) having a longitudinal direction (L) and a transverse direction (T) and comprising a base spring blade (2), an ankle spring blade (3) being made from a composite material comprising glass fibers and a heel spring blade (4), the base spring blade (2) and the ankle spring blade (3) being connected in a forefoot region (5) of the prosthetic foot device (1), the base spring blade (2) and the heel spring blade (4) being connected in a heel region (7) of the prosthetic foot device and the ankle spring blade (3) and the heel spring blade (4) being connected in an ankle region (9) of the prosthetic foot device.

10 Claims, 6 Drawing Sheets

(52) U.S. Cl.
CPC .... *A61F 2/6607* (2013.01); *A61F 2002/5056* (2013.01); *A61F 2002/6621* (2013.01); *A61F 2002/6642* (2013.01); *A61F 2002/6657* (2013.01); *A61F 2002/6664* (2013.01)

(58) Field of Classification Search
CPC ...... A61F 2002/5056; A61F 2002/6614; A61F 2002/6621; A61F 2002/6628; A61F 2002/6635; A61F 2002/6642; A61F 2002/665; A61F 2002/6657; A61F 2002/6664; A61F 2002/6671; A61F 2002/6678; A61F 2002/6685; A61F 2002/6692
See application file for complete search history.

(56) References Cited

U.S. PATENT DOCUMENTS

| | | | |
|---|---|---|---|
| 4,822,363 A | 4/1989 | Phillips | |
| 4,865,612 A | 9/1989 | Arbogast et al. | |
| 5,037,444 A | 8/1991 | Phillips | |
| 5,156,631 A * | 10/1992 | Merlette | A61F 2/60 623/27 |
| 5,219,365 A | 6/1993 | Sabolich | |
| 5,258,039 A | 11/1993 | Goh et al. | |
| 5,509,938 A | 4/1996 | Phillips | |
| 5,800,570 A | 9/1998 | Collier | |
| 5,944,760 A | 8/1999 | Christensen | |
| 5,976,191 A | 11/1999 | Phillips | |
| 6,099,572 A | 8/2000 | Mosler et al. | |
| 6,669,737 B2 | 12/2003 | Mosler et al. | |
| 6,676,370 B2 | 1/2004 | Tiemann | |
| 6,767,370 B1 | 7/2004 | Mosler et al. | |
| 6,863,695 B2 | 3/2005 | Doddroe et al. | |
| 6,929,665 B2 | 8/2005 | Christensen | |
| 6,972,043 B1 | 12/2005 | Biedermann et al. | |
| 7,815,688 B2 | 10/2010 | Wilson | |
| 8,034,121 B2 | 10/2011 | Christensen | |
| 2005/0038525 A1* | 2/2005 | Doddroe | A61F 2/66 623/55 |
| 2006/0212131 A1 | 9/2006 | Curtis | |
| 2007/0100466 A1* | 5/2007 | Allert | A61F 2/66 623/55 |
| 2011/0107581 A1* | 5/2011 | Williams | A61F 2/5044 29/428 |
| 2011/0208323 A1* | 8/2011 | Clausen | A61F 2/6607 623/55 |
| 2013/0261767 A1 | 10/2013 | Kranner et al. | |

FOREIGN PATENT DOCUMENTS

| | | |
|---|---|---|
| JP | H11265960 A | 9/1999 |
| JP | 2007502629 A | 2/2007 |
| JP | 2007503867 A | 3/2007 |
| JP | 2012040379 A | 1/2012 |
| JP | 2013512043 A | 4/2013 |
| RU | 2088180 C1 | 8/1997 |
| WO | 9410942 A1 | 5/1994 |
| WO | 2014/147070 A1 | 9/2014 |

OTHER PUBLICATIONS

Eitel, Justin. Making an Orthotic Carbon-Fiber Footplate with a Flexible Forefoot. O&P Edge Magazine. Sep. 2012.*
International Search Report and the Written Opinion for corresponding International Application No. PCT/SE2015/051059 dated Dec. 30, 2015.

* cited by examiner

PROSTHETIC FOOT DEVICE

This application is a national phase of International Application No. PCT/SE2015/051059 filed Oct. 6, 2015 and published in the English language, and claims priority to SE 1451220-6 filed Oct. 10, 2014.

TECHNICAL FIELD

The disclosure pertains to a prosthetic foot device having a generally triangular configuration and comprising a base spring blade, an ankle spring blade and a heel spring blade, the base spring blade and the ankle spring blade being connected in a forefoot region, the base spring blade and the heel spring blade being connected in a heel region and the ankle spring blade and the heel spring blade being connected in an ankle region. The disclosure also relates to a method for producing a blank for an ankle spring blade for use in a prosthetic foot device.

BACKGROUND

A prosthetic foot is an important part of a leg prosthesis. The prosthetic foot should be able to reliably store and release energy while dynamically flexing and adapting to changing loads to coordinate movements in the foot prosthesis with the muscular action when a user walks, runs, or stands. It is desirable that a prosthetic foot is relatively inexpensive to manufacture, yet can be easily made to fit users of different sizes, be highly functional and durable. In recent years, significant advance has been achieved in the field of prosthetic feet. However, many of the available prosthetic feet are mechanically complex and employ a number of moving parts. While such devices may provide good and reliable performance characteristics, their cost and complexity limit their use and availability in particular in high volume applications and in user communities which do not have a sophisticated technical infrastructure to support and maintain such devices.

To this end it has been proposed to construct prosthetic foot devices comprising one or more spring blades, as set out in U.S. Pat. Nos. 4,865,612, 5,258,039, 6,099,572, 6,669,737, 6,972,043. Although these devices have somewhat overcome the drawbacks of more mechanically complex devices, they still suffer from problems related to the mechanical strength and flexibility of a prosthetic foot device.

Accordingly, as disclosed herein, it is an object to provide a further improved and simplified prosthetic foot.

SUMMARY

The above objective may be achieved by a prosthetic foot device according to claim 1.

The prosthetic foot device as disclosed herein has a longitudinal direction and a transverse direction and comprises a base spring blade, an ankle spring blade and a heel spring blade, the base spring blade and the ankle spring blade being connected in a forefoot region of the prosthetic foot, the base spring blade and the heel spring blade being connected in a heel region of the prosthetic foot and the ankle spring blade and the heel spring blade being connected in an ankle region of the prosthetic foot. The ankle spring blade of the prosthetic foot device is made from a composite material comprising glass fibres.

When seen from a side, the prosthetic foot as disclosed herein may have a modified triangular shape with the spring blades forming the sides of the triangle and the connection regions forming a first lower corner, a second lower corner and a third upper corner. An inner space or cavity is defined between the non-connected parts of the spring blades.

Spring blades for foot prostheses are usually manufactured from composites comprising stacked carbon fibre webs impregnated with a resin binder. It has now been found that by instead using a composite material comprising glass fibres, the ankle spring blade of a prosthetic foot can be made stronger and more resilient than a conventional carbon fibre spring blade. The glass fibres may be provided in the form of woven or nonwoven webs. The webs generally have a specified fibre directionality. By controlling how the webs and thereby the fibres are arranged in a composite material the fibre directionality can be utilized to control the elastic properties in a spring blade.

The glass fibre content in a composite material as disclosed herein may be at least 50% of the total volume of the composite material, and may preferably be at least 60% of the total volume of the composite material, such as 60-90% of the total volume of the composite material.

The ankle spring blades as disclosed herein and comprising glass fibres may be bent or flexed to a higher degree before breaking than a carbon fibre spring blade of the same thickness. The capability of dynamically flexing and twisting in response to changing loads is particularly important in an ankle spring blade, which is the spring blade being subjected to the greatest variations in load during use of the prosthetic foot. In previous ankle spring blade constructions, such as in the construction disclosed in U.S. Pat. No. 6,099,572, multiple spring blades and other components have been used to obtain a required combination of deformability and strength. It has now been found, that satisfactory properties with regard to dynamic deformation, strength and durability may be obtained with a single spring blade comprising glass fibres, which means that a highly functional, light-weight prosthetic foot device can be produced at relatively low cost involving a minimum of components and process steps.

Although good dynamic deformation properties are particularly important in the ankle spring blade, a high capacity for flexing and twisting without rupturing may also be a desired property in a heel spring blade or in a base spring blade.

A further advantage of making spring blades for a prosthetic foot from a glass fibre composite instead of from a carbon fibre composite is that the glass fibre composite may be made in any desirable colour by adding a suitable pigment to the binder component in the composite. It is also possible to use one or more coloured or printed glass fibre webs or decoration webs in the fibre composite.

The ankle spring blade may comprise a forward section, a medial section and a rear section in the longitudinal direction of the prosthetic foot device. The forward section has a first thickness, the medial section has a second thickness and the rear section has a third thickness, the first thickness being smaller than the second thickness and the third thickness and the second thickness being smaller than the third thickness.

Considering the requirement that the thickness of the ankle spring blade decreases in a direction from the forward section to the rear section, the first thickness of the ankle spring blade may be from 2-6 mm, preferably from 3-5.5 mm, such as 4-4.8 mm the second thickness may be from 3-9 mm, preferably from 4-8 mm, such as 5-6 mm and the third thickness may be from 5-10 mm, preferably from 6-9 mm, such as 6-7 mm, wherein "mm" should be read as "millimeters".

The ankle spring blade may be divided into the forward section, the medial section and the rear section along dividing lines extending across the ankle spring blade from a first side edge to a second side edge of the ankle spring blade. A change in thickness between the sections may take place continuously. However, it may be preferred that the change in thickness of the ankle spring blade takes place in discrete steps at one or both of the dividing lines, and preferably within an area at each the dividing line having an extension in the longitudinal direction of from 0 to 3 millimeters of the ankle spring blade.

The dividing lines may have any suitable line shape or combination of line shapes such as a straight line extending diagonally or transversely across the ankle spring blade, or may be forwardly curved, rearwardly curved, have a forwardly or rearwardly directed V-shape, etc. However, it may be preferred that the dividing lines extend in the transverse direction of the ankle spring blade, perpendicular to the longitudinal direction of the ankle spring blade. Transversely extending dividing lines may simplify production of the ankle spring blade as the ankle spring blade may be produced as a continuous composite web extending in a machine direction, MD, and being divided in the cross machine direction CD into three bandshaped areas extending parallel in the MD. A web of this kind may be used as a starting material from which multiple identical ankle spring blades having the required thickness gradient may be cut out.

A thickness gradient as set out herein provides the ankle spring blade with an optimal capacity of adapting and responding to varying loads as a user walks, runs, or stands on the prosthetic foot device. In the prosthetic foot device, the thin forward section of the ankle spring blade is connected to the base spring blade in the forefoot region of the prosthetic foot device. The connection may be made by any suitable connecting means such as by adhesive being applied between the spring blades, by mechanical fastening elements or by welding, with an adhesive connection generally being preferred. Within the connection region, the effective dynamic deformation properties of the prosthetic foot device are dependent on the combined properties of the base spring blade, the ankle spring blade, and the connection means. It is generally desirable that the forefoot region has sufficient flexibility to allow the prosthetic foot device to be tilted somewhat to either side e.g. when a user is walking and puts load on the forefoot region of the prosthetic foot device. Flexibility and resilience in the forefoot region may to some extent be improved by selecting an elastically deformable adhesive for connecting the ankle spring blade with the base spring blade. However, as the forefoot region is a laminate of two spring blades, the resultant stiffness in this region is dependent on the combined stiffness of the laminated spring blades and may be higher than would ideally be desired. By making the forward section of the ankle spring blade thinner than the other two sections, the stiffness of the forefoot region may be reduced while still providing a sufficient area for obtaining a good functional connection between the ankle spring blade and the base spring blade.

The medial section of the ankle spring blade is the section corresponding to the metatarsal part of a natural foot. This section should have the highest ability of dynamical deformation, i.e. of twisting and bending in response to shifting loads.

The rear section of the ankle spring blade is connected to the heel spring blade and may also form part of an attachment arrangement for a connecting device for connecting the prosthetic foot device to a leg prosthesis or to a stump of an amputee. Accordingly, it may be beneficial that the ankle spring blade has a relatively thick rear section providing the attachment site with high torsional and flexural resistance and a firm basis for anchoring a connecting device.

As set out herein, using a glass fibre composite material in a blade spring for a prosthetic foot may be particularly beneficial in an ankle spring blade. However, it is also conceivable that the heel spring blade is made from a composite material comprising glass fibres in order to obtain a heel spring blade with high strength and good flexural and bending properties.

The base spring blade may be made from a composite material comprising carbon fibres or from a composite material comprising glass fibres. The function of the base spring blade is to transfer and distribute forces to and between the other spring blades. The base spring blade is not subjected to torsional and flexural forces of the same magnitude as those arising in the ankle spring blade. Hence, for the base spring, a conventional carbon fibre spring blade may provide sufficient strength and flexibility.

The ankle blade spring may have a width between the side edges which varies in the longitudinal direction of the ankle spring blade. A forward section of the ankle spring blade may comprise a widened toe portion.

It may be preferred that the widened toe portion of the ankle spring blade has a maximum width which is smaller than a corresponding maximum width of the base spring blade in the forefoot region of the prosthetic foot. In other words, the toe portion of the ankle spring blade may be narrower than the front portion of the base spring blade such that the base spring blade extends transversely outside the side edges of the ankle spring blade. Accordingly, in an arrangement of this kind the side portions of the forefoot region of the prosthetic foot device comprises only the base spring blade and not the ankle spring blade. A forefoot region constructed in this manner has side edge portions of relatively higher flexibility than a central portion of the forefoot region and will be more flexible than a forefoot region in which the ankle spring blade and the base spring blade have the same width.

The medial section of the ankle spring blade may have a width in the transverse direction of the ankle spring blade which decreases in a direction from the rear section of the ankle spring blade to the forward section of the ankle spring blade. An ankle spring blade having a medial section with such tapering width profile will be less resistant to flexing and twisting at the front than at the rear.

The ankle spring blade and the heel spring blade may be connected by means of a spacer element which is arranged between the ankle spring blade and the heel spring blade in the ankle region. The spacer element may be made from a fibre composite material, such as a glass fibre composite or a carbon fibre composite, from a polymeric material, or from any other suitable material.

In order to enhance sideways flexibility of the forefoot region and optionally of the metatarsal region of the prosthetic foot device, a slit may be arranged in the ankle spring blade and may extend in the longitudinal direction from a front end edge of the ankle spring blade through the forward section and optionally into the medial section of the ankle spring blade. The slit can extend through the full length of the medial section of the ankle spring blade and/or through the forefoot region of the base spring blade.

The ankle spring blade may comprise a laminate comprising stacked layers of glass fibre web material and binder material. The glass fibre web material may be a weft material and the binder material may be a resinous binder material such as an epoxy resin binder. The stacked glass fibre webs may be impregnated by or embedded in the binder material or the binder material may be applied as coatings or layers between the stacked layers of glass fibre web material to form a consolidated composite material comprising the glass fibre web material and the binder material. As set out herein, the composite spring blade material may comprise further components, such as pigments, printed/coloured webs or films, decorative objects, etc.

A laminated composite ankle spring blade may comprise:
- 1-5 bottom layers of the glass fibre web material, the bottom layer or bottom layers extending the full length of the ankle spring blade;
- 1-5 middle layers of the glass fibre web material, the middle layer or middle layers extending only over the medial section and the rear section of the ankle spring blade; and
- 1-5 top layers of the glass fibre web material, the top layer or top layers extending only over the rear section of the ankle spring blade.

The prosthetic foot device as disclosed herein may further comprise a connecting device, the connecting device being attached to the ankle spring blade within the ankle region of the prosthetic foot device. The connecting device is configured to be used for coupling the prosthetic foot device to a prosthetic leg and/or to a stump of an amputee and may be made from metal, plastic or any other suitable material or composite material.

A method of manufacturing an ankle spring blade as disclosed herein may comprise the steps of:
a) forming a glass fibre composite web by
stacking 1-5 bottom layers of elongated glass fibre web material, to form a bottom web portion of the glass fibre composite material, the bottom web portion having a first and a second side edge extending parallel in a longitudinal direction of the glass fibre composite web and a first width between the side edges of the bottom web portion in a transverse direction of the glass fibre composite web;
stacking 1-5 middle layers of elongated glass fibre web material over the bottom web portion, to form a middle web portion of the glass fibre composite material, the middle web portion having a first and a second side edge extending parallel in the longitudinal direction, the first side edge of the middle web portion being made to coincide with the first side edge of the bottom web portion, the middle web portion having a second width in the transverse direction between the middle web side edges, the second width being smaller than the first width;
stacking 1-5 top layers of elongated glass fibre web material over the middle web portion, to form a top web portion of the glass fibre composite material, the top web portion having a first and a second side edge extending parallel in the longitudinal direction, the first side edge of the top web portion being made to coincide with the first side edge of the bottom web portion and the middle web portion, the middle web portion having a third width in the transverse direction between the top web side edges, the third width being smaller than the first width and the second width impregnating the stacked glass fibre web material with a curable binder; and
curing the binder;
b) cutting out ankle spring blade blanks from the glass fibre composite web with a longitudinal direction of the ankle spring blade blanks coinciding with the transverse direction of the glass fibre composite web.

A method as set out above allows for efficient and reliable production of multiple ankle spring blades having sections of different thickness. The method may comprise further steps such as the addition of further material layers, pigments, etc. as set out herein. The spring blade blanks may be further processed by polishing, by applying a surface finish or coating, by printing, by cutting out a slit, by rounding off sharp edges and corners, by making holes for attaching a coupling device, etc.

An ankle spring blade produced according to the method as set out above may be used for producing a prosthetic foot device as disclosed herein by connecting the ankle spring blade to a base spring blade in a forefoot region of the prosthetic foot device, connecting a heel spring blade to the base spring blade in a heel region of the prosthetic foot device and connecting the ankle spring blade and the heel spring blade in an ankle region of the prosthetic foot device. The prosthetic foot device may be further provided with a connecting device for connecting the prosthetic foot device to a leg prosthesis or to a stump of an amputee. The connecting device is attached to the ankle spring blade within the ankle region of the prosthetic foot device.

BRIEF DESCRIPTION OF THE DRAWINGS

The invention will be described in greater detail below with reference to the figures shown in the appended drawings. It should be understood that he figures are schematic illustrations and that they are not necessarily drawn to scale.

DETAILED DESCRIPTION

Figure 1:
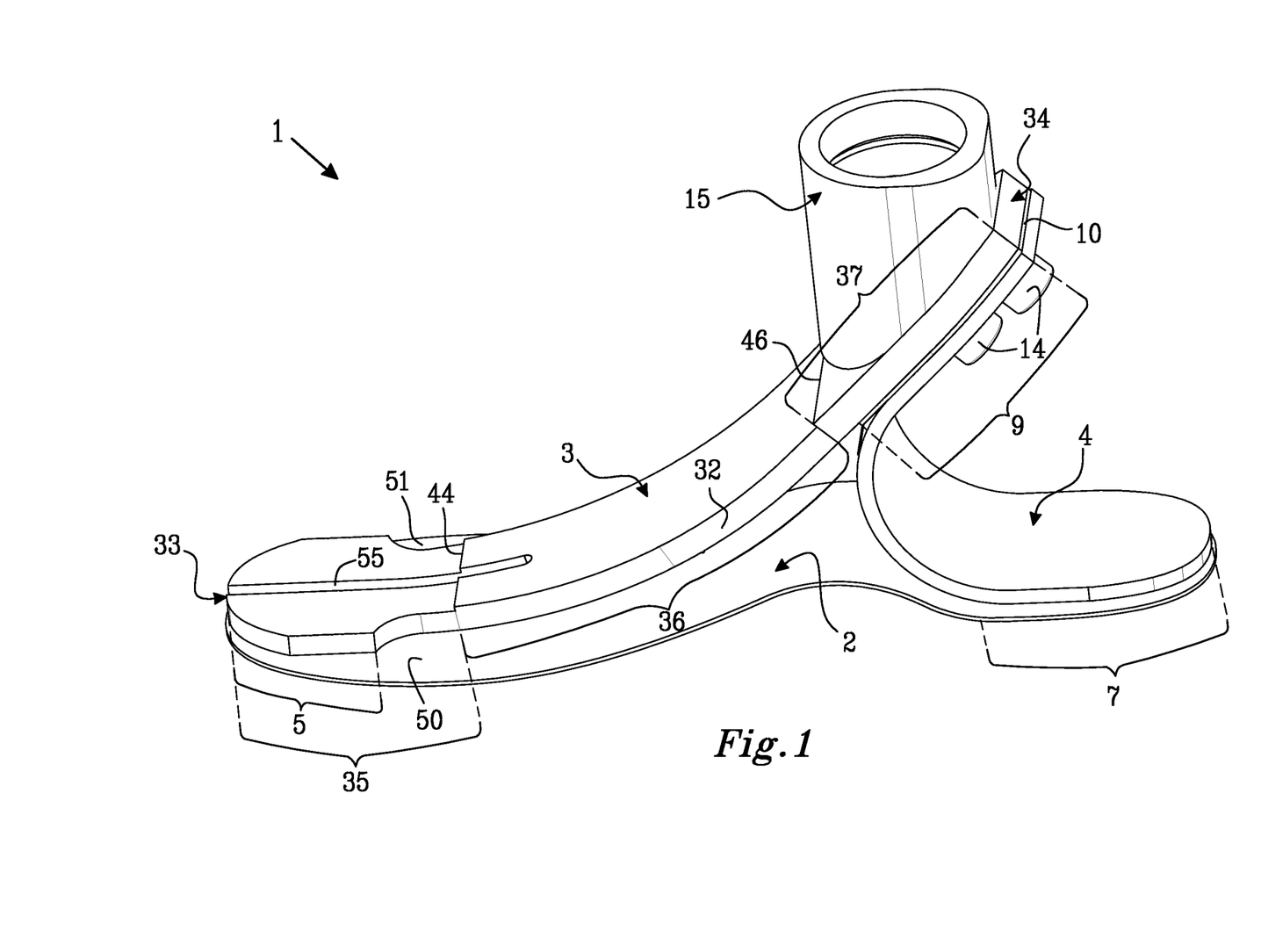
FIG. 1 shows a perspective view of a prosthetic foot device according to the invention.
Figure 2:
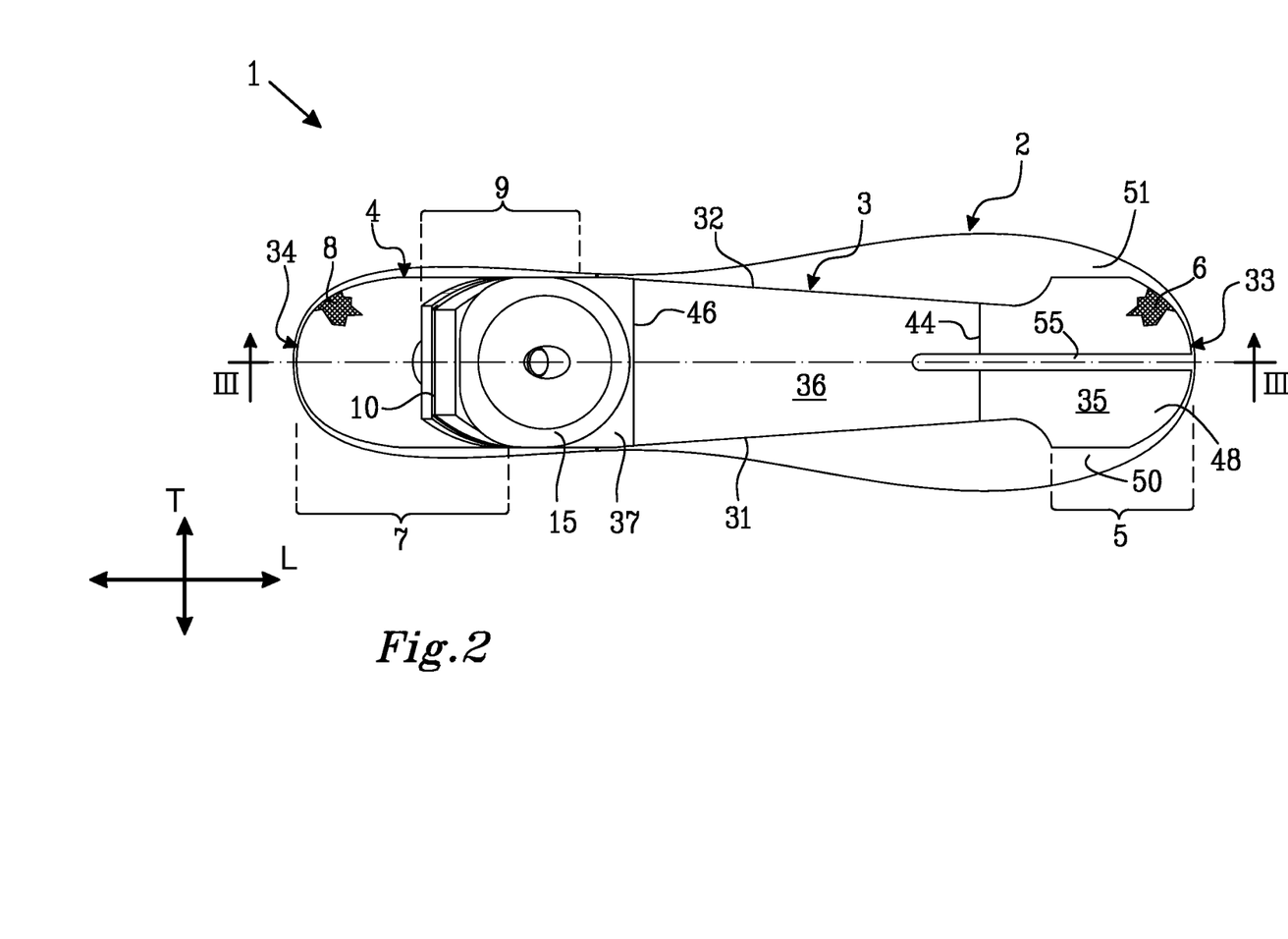
FIG. 2 shows a top view of the prosthetic foot device in FIG. 1.
Figure 3:
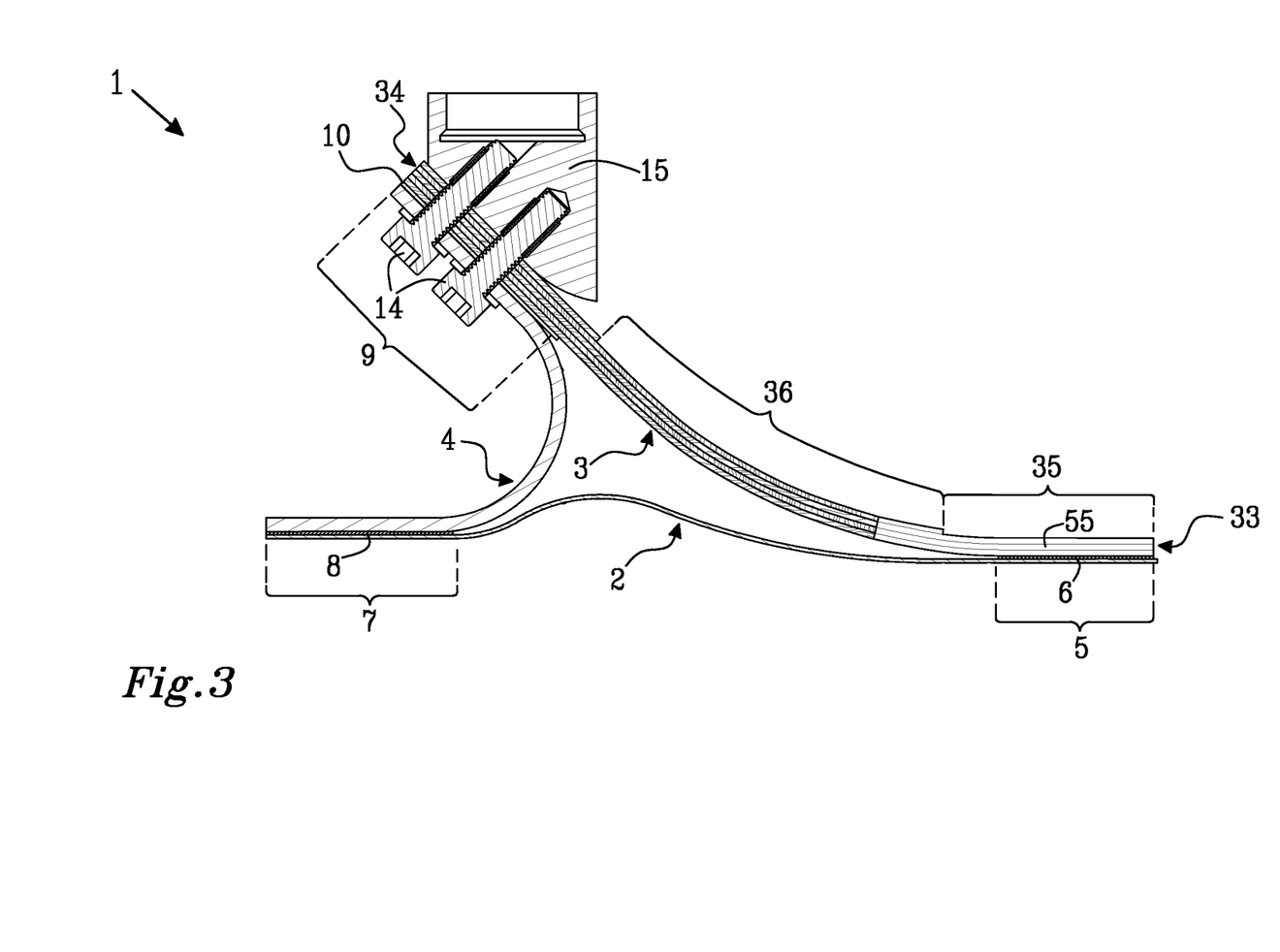
FIG. 3 shows a cross-sectional view of the prosthetic foot device taken along the line III-III in FIG. 2.
Figure 4:
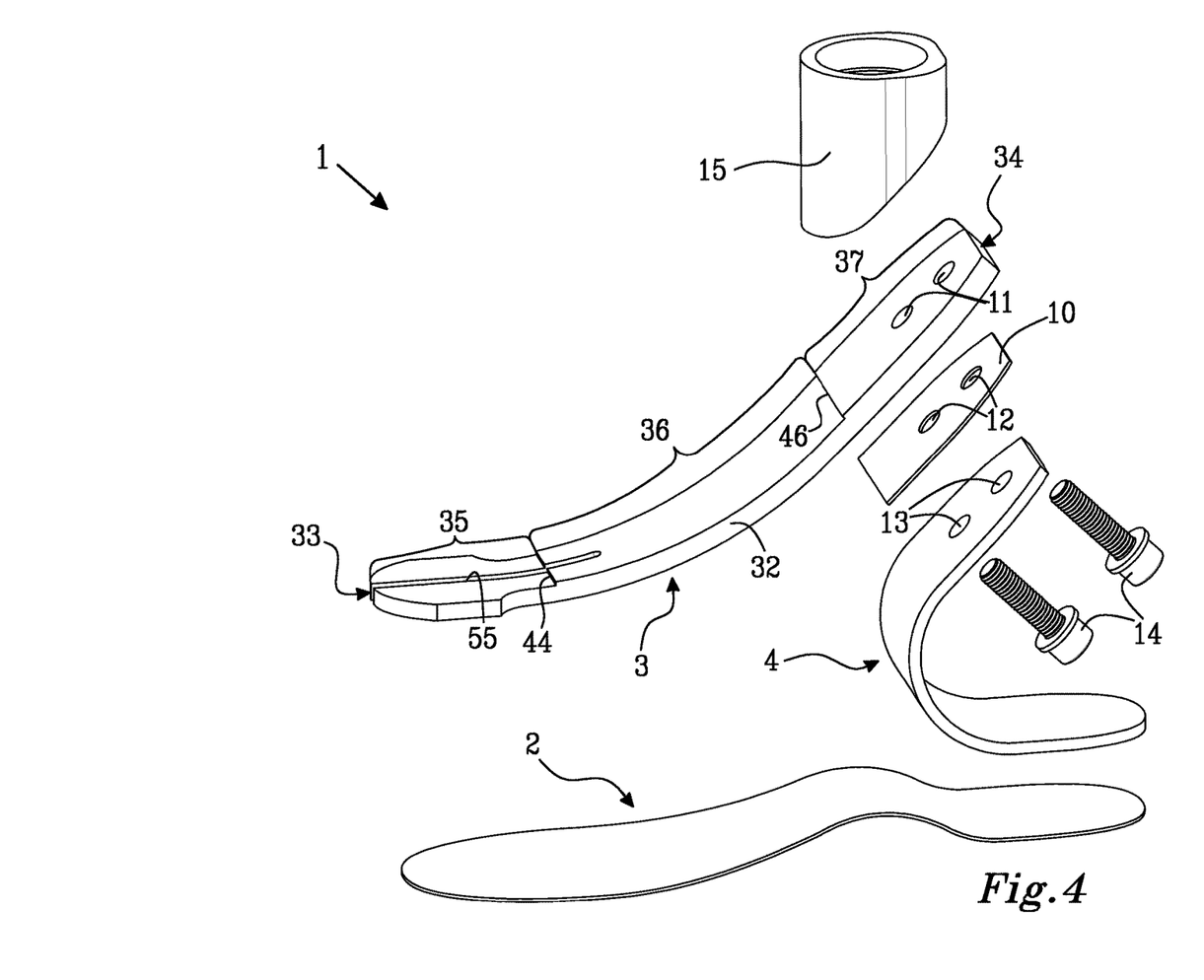
FIG. 4 shows an exploded perspective view of the prosthetic foot device in FIG. 1.

FIGS. 1-4 show a prosthetic foot device 1 comprising a base spring blade 2, an ankle spring blade 3 and a heel spring blade 4. The base spring blade 2 and the ankle spring blade 3 are connected in a forefoot region 5 of the prosthetic foot device 1 by means of a first adhesive 6 applied between the ankle spring blade 3 and the heel spring blade 4, as indicated in FIG. 3. The base spring blade 2 and the heel spring blade 4 are similarly connected in a heel region 7 of the prosthetic foot device 1 by means of a second adhesive 8 applied between the base spring blade 2 and the heel spring blade 4. The first and second adhesives may be of the same kind or may be adhesives with different properties. By way of example, the adhesive in the forefoot region 5 may be more elastic and/or flexible than the adhesive in the heel region 7 thereby providing a more flexible connection in the forefoot region 5 and a stiffer connection in the heel region 7. Optionally, the first adhesive 6 and/or the second adhesive 8 may be substituted with any other suitable type of connection means including mechanical connections means such as screws and rivets and welds. In such constructions it may be desirable to arrange a resiliently deformable member such as a resilient polymer layer between the spring blades. The ankle spring blade 3 and the heel spring blade 4 are connected with each other in an ankle region 9 of the prosthetic foot device 1. The connection between the ankle spring blade 3 and the heel spring blade 4 is an indirect connection involving a spacer element 10 which is arranged between the ankle spring blade 3 and the heel spring blade 4 in the ankle region 9. The spacer element 10 is shown in FIG. 4 as having generally the same shape as the ankle spring blade 3 and the heel spring blade 4 within the ankle region 9 and to have a length $l_s$ with a major component in the longitudinal direction L of the prosthetic foot device 1, which length $l_s$ corresponds to the length of the ankle region 9. Hence, the spacer element 10 is considerably shorter than both the ankle spring blade 3 and the heel spring blade 4.

A pair of attachment openings 11,12,13 are arranged through each of the ankle spring blade 3, the spacer element 10 and the heel spring blade 4 within the ankle region 9. 11,12,13. As shown in FIG. 4, the attachment openings 11,12,13 are arranged centrally in the longitudinal direction L of the prosthetic foot device 1. When the prosthetic foot device 1 is assembled, as shown in FIG. 1, the attachment openings 11,12,13 are aligned with each other and a screw bolt 14 is inserted through each attachment opening 11,12,13 and secured in a connecting device 15, for connecting the prosthetic foot device 1 with a leg prosthesis and/or the stump of an amputee. It is to be understood that the design of the connecting device is not critical to the invention and that a connecting device may be secured to the heel region of the prosthetic foot device by other means than the two screw bolts shown in the drawings. Accordingly, the connection device may optionally be secured to the prosthetic foot device by any suitable means or combination of means such as by welding, gluing, or by any suitable type of mechanical fastening elements. Similarly, the connection between the ankle spring blade 3 and the heel spring blade 4 may be an adhesive connection, a welded connection or another type of mechanical connection than the connection shown in the figures, as well as combinations of different connection means. The spacer element 10 may be omitted or may be replaced by an adhesive applied between the ankle spring blade 3 and a heel spring blade 4 in the heel region 9.

The ankle spring blade 3 has a concave curve shape in the longitudinal direction L of the prosthetic foot device 1, and a generally planar shape in a transverse direction T of the prosthetic foot device 1, perpendicular to the longitudinal direction L. The ankle spring blade 3 has a generally elongated shape with two side edges 31, 32 extending in the longitudinal direction L between a forefoot end 33 and a rear end 34.

The ankle spring blade is made from a composite material comprising glass fibres. As is shown in FIG. 3, the ankle spring blade is made from a laminate comprising stacked layers of glass fibre web material and binder material. The ankle spring blade 3 comprises a forward section 35, a medial section 36 and a rear section 37 in the longitudinal direction L of the prosthetic foot device 1. As indicated in FIGS. 5a and 5b which show cross-sections of the ankle spring blade 3 in a flat configuration before mounting in a prosthetic foot device and in the bent configuration in which it appears when mounted in the prosthetic foot device 1, the forward section 35 has a first thickness $t_f$, the medial section 36 has a second thickness $t_m$ and the rear section 37 has a third thickness $t_r$, such that the first thickness $t_f$ is smaller than the second thickness $t_m$ and the third thickness $t_r$, and wherein the second thickness $t_m$ is smaller than the third thickness $t_r$ according to the relation:

$$t_f < t_m < t_r$$

Figure 5A:
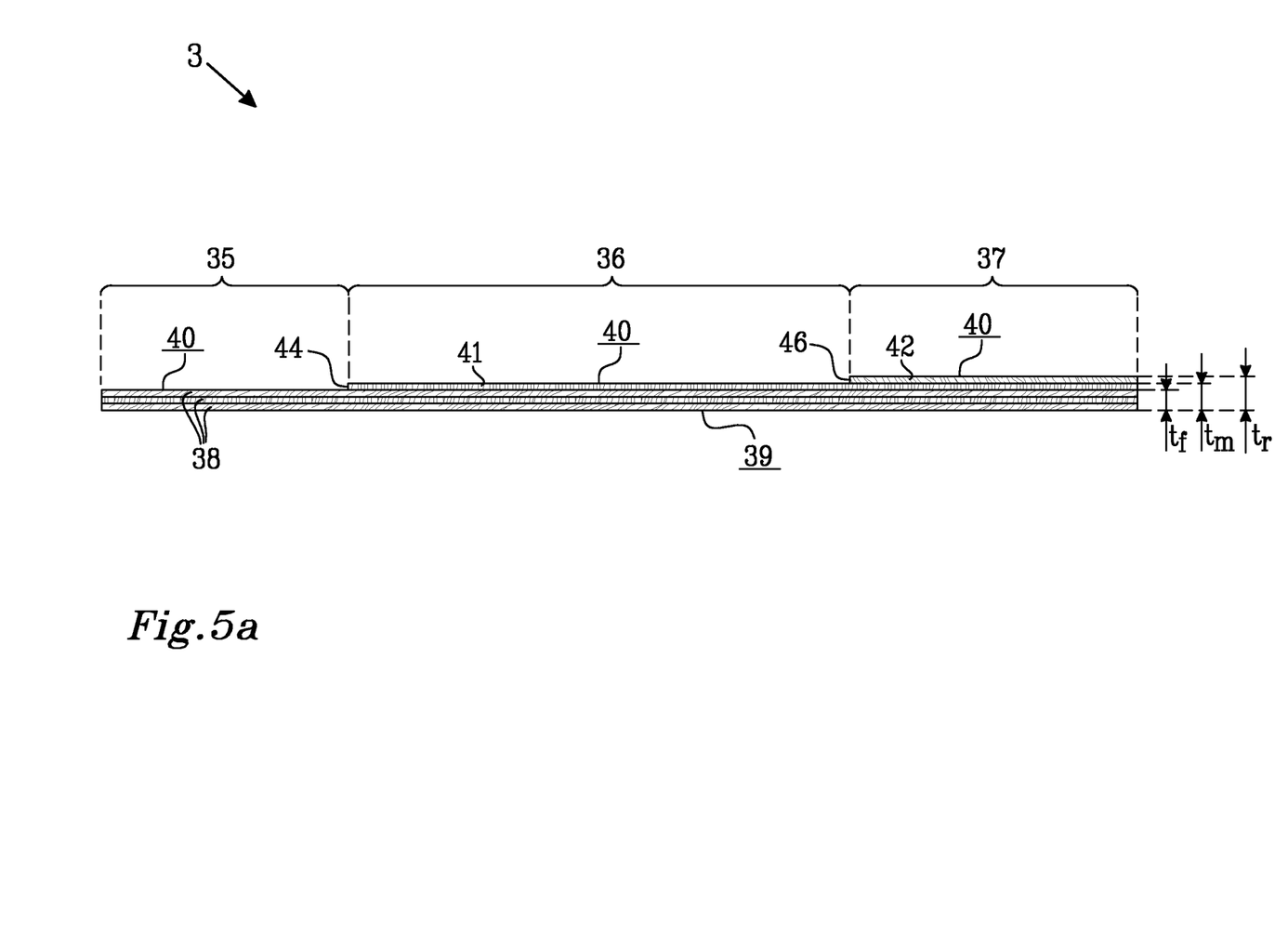
FIGS. 5a and 5b show a side view of an ankle spring blade for use in a prosthetic foot device in accordance with the invention.
Figure 5B:
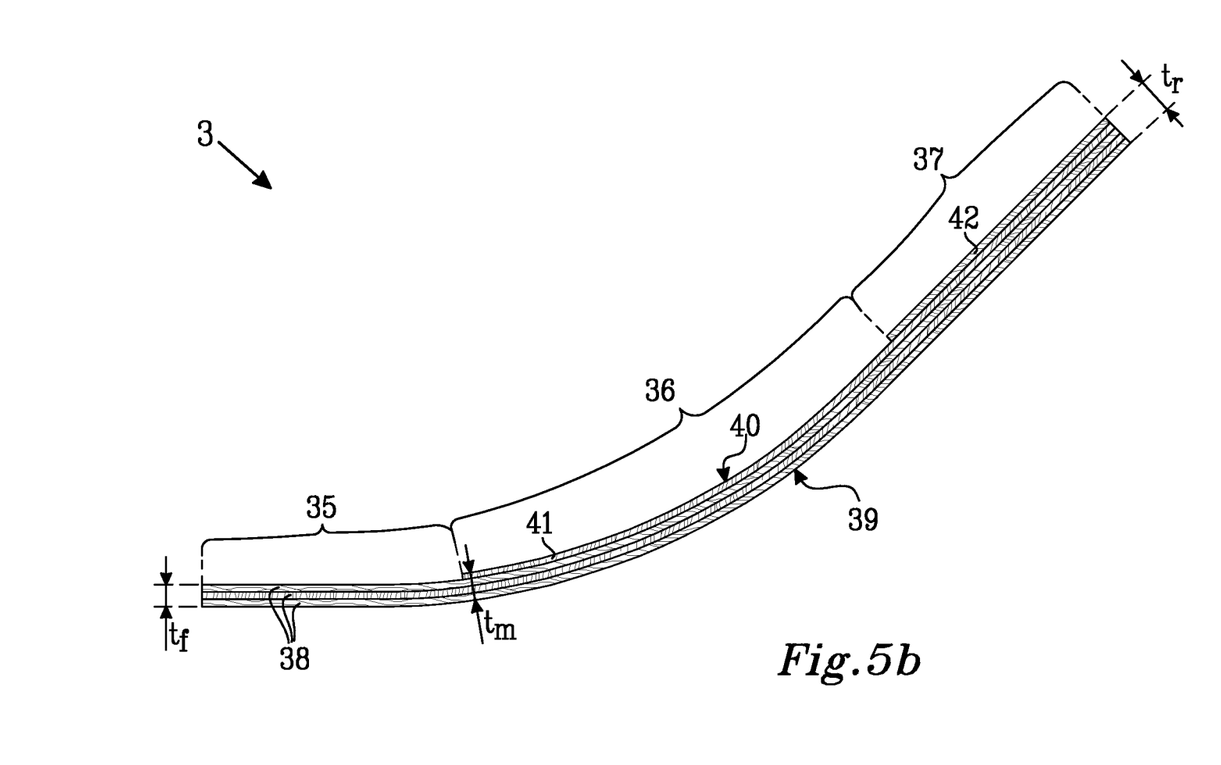

As schematically shown in FIGS. 5a and 5b, the ankle spring blade 3 comprises 1-5 bottom layers 38 of glass fibre web material. The bottom layers 38 extend the full length of the ankle spring blade 3 and define the longitudinal extension of the ankle spring blade 3. A lowermost bottom layer also forms an inner surface 38 of the ankle spring blade 3, which inner surface 39 is facing the base spring blade 2 in the forefoot region 5 and the heel spring blade 4 in the heel region 7. The inner surface 40 of the ankle spring blade 3 is opposite an outer surface 39 of the ankle spring blade 3, which outer surface faces away from the base spring blade 3 and the heel spring blade 4. The combined thickness of the bottom layers 38 of the ankle spring blade 3 corresponds to the first thickness $t_f$ of the forward section 35 of the ankle spring blade 3.

The ankle spring blade 3 further comprises 1-5 middle layers 41 of glass fibre web material, the middle layer or middle layers 41 extending only over the medial section 36 and the rear section 37 of the ankle spring blade and 1-5 top layers 42 of glass fibre web material, the top layer or top layers 42 extending only over the rear section of the ankle spring blade. The combined thickness of the bottom layers 38 and the middle layers 41 of the ankle spring blade 3 corresponds to the second thickness $t_m$ of the middle section 36 of the ankle spring blade 3 and the combined thickness of the bottom layers 38, the middle layers 41 and the top layers 42 of the ankle spring blade 3 corresponds to the third thickness $t_r$ of the rear section 37 of the ankle spring blade 3.

The length proportions between the different sections of an ankle spring blade as disclosed herein may be such that the front section is approximately 25% of the total length of the ankle spring blade, the length of the medial section is approximately 50% of the total length of the ankle spring blade and the length of the rear section is approximately 25% of the total length of the ankle spring blade. However, the length of the front section may be between 15% and 30% of the total length of the ankle spring blade, the length of the medial section may be from 40% to 70% of the total length of the ankle spring blade and the length of the rear section may be from 15% to 35% of the total length of the ankle spring blade. The rear section may be somewhat longer than the front section. The proportions between the different sections may vary depending on the size and weight of the intended user, and/or depending on the intended use situations as set out herein.

By way of example only, in a prosthetic foot device for an adult, an ankle spring blade having a total length of 215 millimeters, the front section may be 50 millimeters, the medial section may be 105 millimeters and the rear section may be 60 millimeters. For longer or shorter ankle spring blades, the measurements for the individual sections will, of course, be different.

The glass fibre web material may be a weft material and the binder material may be a resinous binder material such as an epoxy resin binder. The stacked glass fibre webs may be impregnated by or embedded in the binder material or the binder material may be applied as coatings or layers between the stacked layers of glass fibre web material to form a consolidated composite material comprising the glass fibre web material and the binder material. As set out herein, the composite spring blade material may comprise further components, such as pigments, printed/coloured webs or films, decorative objects, etc. and may be coated or laminated with an outer covering film or web on one or both of the outer surfaces of the fibre composite material.

The first thickness, i.e. the thickness of the forward section of the ankle spring blade 3 may be from 2-6 mm, preferably from 3-5.5 mm, the second thickness, i.e. the thickness of the medial section may be from 3-9 mm, preferably from 4-8 mm and the third thickness may be from 5-10 mm, preferably from 6-9 mm, taking into consideration that the thickness relation between the different sections as set out above should always apply.

The ankle spring blade is divided into the forward section 35, the medial section 36 and the rear section 37 along dividing lines 44, 46 extending across the ankle spring blade 3 from one side edge 31 to the other side edge 32 of the ankle spring blade 3. The change in thickness between the sections 35, 36, 37 of the ankle spring blade 3 is shown to take place abruptly at the dividing lines 44, 46, preferably within an area at each dividing line having an extension in the longitudinal direction of from 0 to 3 millimeters of the ankle spring blade 3. The abrupt thickness change can be obtained as illustrated in FIGS. 5a and 5b by stacking glass fibre webs 38, 41, 42 of different lengths on top of each other. The change in thickness will be visible as a stepped surface profile on the outer surface 40 of the ankle spring blade 3. Although the dividing lines 44, 46 may take on other shapes than the straight transverse lines shown in the figures, such as V-shapes, U-shapes, etc, as set out herein, it has been found that straight and distinct transverse dividing lines may be preferred over other types of dividing lines or dividing areas both for functional reasons and for production reasons. Without wishing to be bound by theory, a distinct border between the different sections 35, 36, 37 of the ankle spring blade 3, may promote a differentiation between the different functions of the different sections 35, 36, 37. Accordingly, the main function of the forward section 35 of the ankle spring blade 3 is to provide a connection surface for connecting the ankle spring blade 3 with the base spring blade 2 within the forefoot region 9, while making a minimum contribution to the stiffness of the forefoot region 9. The medial section 36 should have high capability of dynamically deforming by resiliently twisting and bending in response to varying loads, similar to the movements occurring in the metatarsal region of a natural foot. The rear section 37 should provide a stiff and firm anchoring site for the connecting device 15.

The ankle spring blade 3 is shown, e.g. in FIG. 2 with a "hammerhead shape", which means that it has a widened toe portion 48 in the forward section 35 of the ankle spring blade 3 and a more narrow forwardly tapering medial portion 36. The widened toe portion 48 provides an enlarged connection surface for connecting the ankle spring blade 3 with the base spring blade 4 and the tapering medial portion 36 provides the requisite torsional and bending characteristics in the metatarsal part of the prosthetic foot device 1.

As is best seen in FIG. 2, the maximum width of the widened toe portion 48 of the ankle spring blade 3 is smaller than the maximum width of the base spring blade 2 in the forefoot region of the prosthetic foot device. In this way, side portions 50, 51 of the base spring blade 2 extend laterally outside the ankle spring blade 3 in the forefoot region 5. This means that the forefoot region 5 is more flexible within the area formed only by the side portions 50, 51 of the base spring blade 2 than in the part of the forefoot region 5 where the ankle spring blade 3 and the construction adhesive 6 are also present. A forefoot region 5 constructed in this manner will be less rigid and will have higher sideways flexibility than a forefoot region in which the ankle spring blade and the base spring blade have the same width.

As set out above, the medial section 36 of the ankle spring blade 3 has a tapering shape implying that the width of the ankle spring blade 3 in the transverse direction T decreases in a direction from the rear section 37 of the ankle spring blade 3 to the forward section 35 of the ankle spring blade 3. An ankle spring blade having a medial section 36 with a width profile of this kind will be less resistant to flexing and twisting at the front than at the rear.

It is to be understood that the tapering shape of the ankle spring blade, as well as the widened toe portion and different widths of the ankle spring blade and the base spring blade in the forefoot region are optional to the invention. Accordingly, the ankle spring blade may have the same width along its full longitudinal extension. Moreover, a widened toe portion may have the same maximum width as the base spring blade and/or may be combined with a straight or tapering medial section, as desired.

It is to be understood that the lateral shape of the ankle spring blade as well as the use of features such as sections of different thickness, a widened toe portion, etc. may be varied within the scope of the invention depending to suit particular user requirements. A prosthetic foot device may be designed to suit a particular individual and/or a particular use situation. By way of example, a heavier user may need an overall thicker ankle spring blade, a prosthetic foot device intended for high activity purposes may be designed to allow more flexing and bending than a prosthetic foot device intended for an every-day use, where a more rigid and stable prosthetic foot device may be preferred.

In the drawings, the prosthetic foot device 1, is shown with a slit 55 being arranged in the ankle spring blade 3 and extending in the longitudinal direction L from the front end edge 33 of the ankle spring blade 3 through the forward section 35 and a small distance into the medial section 36 of the ankle spring blade. The slit 55 is an optional feature of the invention and may be omitted, if desired. The slit 55 increases sideways flexibility in the forefoot region 5 of the prosthetic foot device 1 and if extended into the medial section 36 it will also decrease torsional resistance in the metatarsal part of the prosthetic foot device 1. If desired, the slit can extend through all of the medial section 36 of the ankle spring blade 3 and/or through the forefoot region 5 of the base spring blade 2.

As set out herein, the heel spring blade may be made from a composite material comprising carbon fibres or from a composite material comprising glass fibres, as desired.

Likewise, the base spring blade 2 may be made from a composite material comprising carbon fibres or from a composite material comprising glass fibres, as desired.

The invention claimed is:

1. A prosthetic foot device having a longitudinal direction and a transverse direction and comprising a base spring blade, an ankle spring blade and a heel spring blade, said base spring blade and said ankle spring blade being connected in a forefoot region of said prosthetic foot device, said base spring blade and said heel spring blade being connected in a heel region of said prosthetic foot device and said ankle spring blade and said heel spring blade being connected in an ankle region of said prosthetic foot device, said ankle spring blade being made from a composite material comprising glass fibers, wherein said ankle spring blade comprises a forward section, a medial section and a rear section in said longitudinal direction of said prosthetic foot device, said forward section having a first thickness, said medial section having a second thickness and said rear section having a third thickness, wherein said first thickness is smaller than said second thickness and smaller than said third thickness and wherein said second thickness is smaller than said third thickness said ankle spring blade being divided into said forward section, said medial section and said rear section along dividing lines extending across said ankle spring blade from a first side edge to a second side edge of said ankle spring blade and wherein a change in thickness between said sections of said ankle spring blade takes place abruptly at said dividing lines, wherein said ankle spring blade comprises a laminate comprising stacked layers of glass fiber web material and binder material, wherein said ankle spring blade comprises:
- 1-5 bottom layers of said glass fiber web material, said bottom layer or bottom layers extending the full length of said ankle spring blade;
- 1-5 middle layers of said glass fiber web material, said middle layer or middle layers extending only over said medial section and said rear section of said ankle spring blade; and
- 1-5 top layers of said glass fiber web material, said top layer or top layers extending only over said rear section of said ankle spring blade.

2. A prosthetic foot device according to claim 1, wherein said first thickness is from 2-6 mm, said second thickness is from 3-9 mm, and said third thickness is from 5-10 mm.

3. A prosthetic foot device according to claim 1, wherein said dividing lines extend in said transverse direction, perpendicular to said longitudinal direction of said prosthetic foot device.

4. A prosthetic foot device according to claim 1, wherein said heel spring blade is made from a composite material comprising glass fibers.

5. A prosthetic foot device according to claim 1, wherein said base spring blade is made from a composite material comprising carbon fibers.

6. A prosthetic foot device according to claim 1, wherein said forward section of said ankle spring blade comprises a widened toe portion.

7. A prosthetic foot device according to claim 6, wherein a maximum width of said widened toe portion of said ankle spring blade is smaller than a maximum width of said base spring blade in said forefoot region of said prosthetic foot device.

8. A prosthetic foot device according to claim 1, wherein said medial section of said ankle spring blade has a width in said transverse direction of said prosthetic foot device, said width of said medial section of said ankle spring blade decreasing in a direction from said rear section of said ankle spring blade to said forward section of said ankle spring blade.

9. A prosthetic foot device according to claim 1, wherein said ankle spring blade and said heel spring blade are connected by a spacer element being arranged between said ankle spring blade and said heel spring blade in said ankle region.

10. A prosthetic foot device according to claim 1, wherein said prosthetic foot device comprises a connecting device, said connecting device being attached to said ankle spring blade within said ankle region of said prosthetic foot device.

* * * * *